United States Patent [19]

Kikuchi et al.

[11] Patent Number: 5,098,809
[45] Date of Patent: Mar. 24, 1992

[54] ELECTROPHOTOGRAPHIC PHOTOSENSITIVE MEMBER CONTAINING A SUBSTITUTED FLUORINE COMPOUND

[75] Inventors: Toshihiro Kikuchi; Akihiro Senoo, both of Yokohama; Tetsuro Kanemaru, Tokyo; Ryoji Yashiro, Fuchu, all of Japan

[73] Assignee: Canon Kabushiki Kaisha, Tokyo, Japan

[21] Appl. No.: 502,225

[22] Filed: Feb. 28, 1990

[30] Foreign Application Priority Data

Mar. 3, 1989 [JP] Japan .................................. 1-51624

[51] Int. Cl.$^5$ .............................................. G03G 5/09
[52] U.S. Cl. ........................................ 430/73; 430/83; 430/95
[58] Field of Search .................... 430/58, 59, 72, 73, 430/83, 95

[56] References Cited

U.S. PATENT DOCUMENTS

| 4,046,564 | 9/1977 | Turner et al. | 430/96 |
| 4,245,021 | 1/1981 | Kazami et al. | 430/58 |
| 4,853,308 | 8/1989 | Ong et al. | 430/73 |
| 4,931,371 | 6/1990 | Matsumoto et al. | 430/59 |
| 4,963,450 | 10/1990 | Miyazaki et al. | 430/59 |

FOREIGN PATENT DOCUMENTS

| 4188 | 1/1977 | Japan . |
| 151955 | 11/1979 | Japan . |
| 42380 | 3/1980 | Japan . |
| 52063 | 4/1980 | Japan . |
| 22437 | 3/1981 | Japan . |
| 195254 | 11/1982 | Japan . |
| 32372 | 2/1983 | Japan . |
| 198043 | 11/1983 | Japan . |
| 208054 | 9/1987 | Japan . |

*Primary Examiner*—John Goodrow
*Attorney, Agent, or Firm*—Fitzpatrick, Cella, Harper & Scinto

[57] ABSTRACT

An electrophotographic photosensitive member comprises a conductive support and a photosensitive layer provided thereon. The photosensitive layer contains a fluorene compound represented by the following Formula (I):

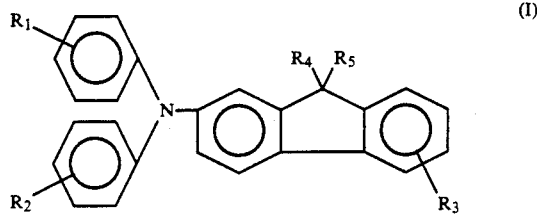

wherein $R_1$ and $R_2$ each represent an alkyl group; $R_3$ represents a hydrogen atom, an alkyl group, an alkoxy group or a halogen atom; $R_4$ and $R_5$ each represent a hydrogen atom, an alkyl group, an aralkyl group or an aryl group.

7 Claims, 2 Drawing Sheets

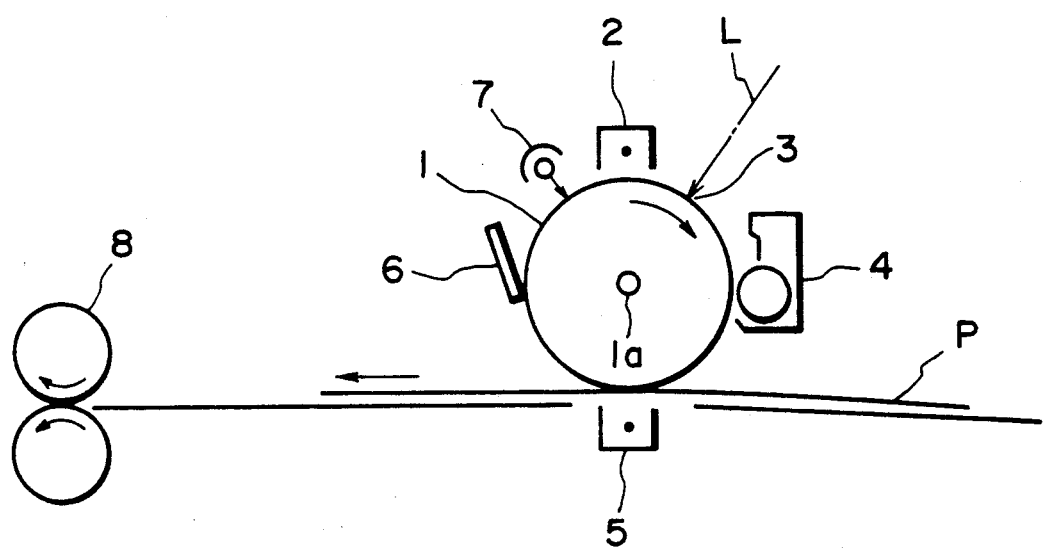
F I G. 2

ELECTROPHOTOGRAPHIC PHOTOSENSITIVE MEMBER CONTAINING A SUBSTITUTED FLUORINE COMPOUND

BACKGROUND OF THE INVENTION

1. Field of the Invention

The present invention relates to an electrophotographic photosensitive member. More particularly, it relates to an electrophotographic photosensitive member comprising a low-molecular organic photoconductive material that can impart improved electrophotographic performances.

2. Related Background Art

Organic photosensitive members comprising a photosensitive layer mainly composed of an organic photoconductive compound have a number of advantages compared with inorganic photosensitive members, and a great number of proposals have been made thereon and have been put into practical use.

An electrophotographic photosensitive member comprising a photosensitive layer mainly composed of a photoconductive polymer as typified by poly-N-vinyl carbazole and a charge-moving complex formed of the photoconductive polymer and a Lewis acid such as 2,4,7-trinitro-9-fluorenone has been proposed as the organic photosensitive member of the type mentioned above. Compared with inorganic photoconductive materials, organic photoconductive polymers of such a type are advantageous in lightness in weight film-forming properties and so forth. They, however, are inferior to the inorganic photoconductive materials in respect of sensitivity, durability, and stability against environmental changes, and hence can not always be satisfactory.

On the other hand, function-separated electrophotographic photosensitive members, having the charge-generating function and charge-transporting function respectively assigned to separate substances, have remarkably improved the sensitivity and durability in which the conventional organic photosensitive members have been considered defective. Such function-separated photosensitive members have the advantages that the materials for the respective charge-generating material and charge-transporting material can be selected in a vast range and an electrophotographic photosensitive member having any desired performance can be prepared with relative ease.

Various azo pigments, polycyclic quinone pigments, cyanine coloring matters, squaric acid dyes, pyrylium salts coloring matters, etc. are known as the charge-generating material. Of these, the azo pigments have a strong light-resistance, a great charge-generating power and can be readily synthesized. In view of these, those having various structures have been proposed.

On the other hand, known charge-transporting material are, for example, pyrazoline compounds as disclosed in Japanese Patent Publication No. 52-4188, hydrozone compounds as disclosed in Japanese Patent Publication No. 55-42380 and Japanese Patent Application Laid-Open No. 55-52063, triphenylamine compounds as disclosed in Japanese Patent Application Laid-Open No. 57-195254 and Japanese Patent Publication No. 58-32372, fluorene compounds as disclosed in Japanese Patent Application Laid-Open No. 50-22437 and No. 62-208054, and stilbene compounds as disclosed in Japanese Patent Application Laid-Open No. 54-151955 and No. 58-198043. What are required for these charge-transporting materials are that (i) they ere stable to light and heat, (ii) they are stable to ozone, $NO_x$, nitric acid, etc. that are generated as a result of corona discharge, (iii) they have a high charge-transporting power. (iv) they have a high compatibility with organic solvents and binders, and (v) they can be readily prepared and are inexpensive. However, although the charge-transporting materials comprising the conventional low-molecular organic compounds can satisfy some of the above requirements, none of them can satisfy all of the requirements on a high level. Thus, there remains room for further improvements.

SUMMARY OF THE INVENTION

Accordingly, an object of the present invention is to provide an electrophotographic photosensitive member employing an organic photoconductive compound that satisfies the performance required in a charge-generating material, thereby eliminating the various disadvantages involved in the prior art.

Another object of the present invention is to provide an electrophotographic photosensitive member having a high sensitivity and capable of stably retaining potential during the repeated use of the member.

A further object of the present invention is to provide an electrophotographic photosensitive member employing a novel organic photoconductive compound that can be prepared with ease and supplied at a moderate price.

The present invention provides an electrophotographic photosensitive member comprising a conductive support and a photosensitive layer provided thereon, wherein said photosensitive layer contains a fluorene compound represented by the following Formula (I):

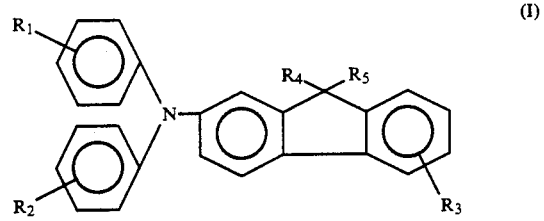

wherein $R_1$ and $R_2$ each represent an alkyl group; $R_3$ represents a hydrogen atom, an alkyl group, an alkoxy group or a halogen atom; $R_4$ and $R_5$ each represent a hydrogen atom, an alkyl group, an aralkyl group or an aryl group.

BRIEF DESCRIPTION OF THE DRAWINGS

FIG. 2 schematically illustrates a common example for the constitution of an electrophotographic apparatus in which a drum photosensitive member is used.

DESCRIPTION OF THE PREFERRED EMBODIMENTS

Figure 1:
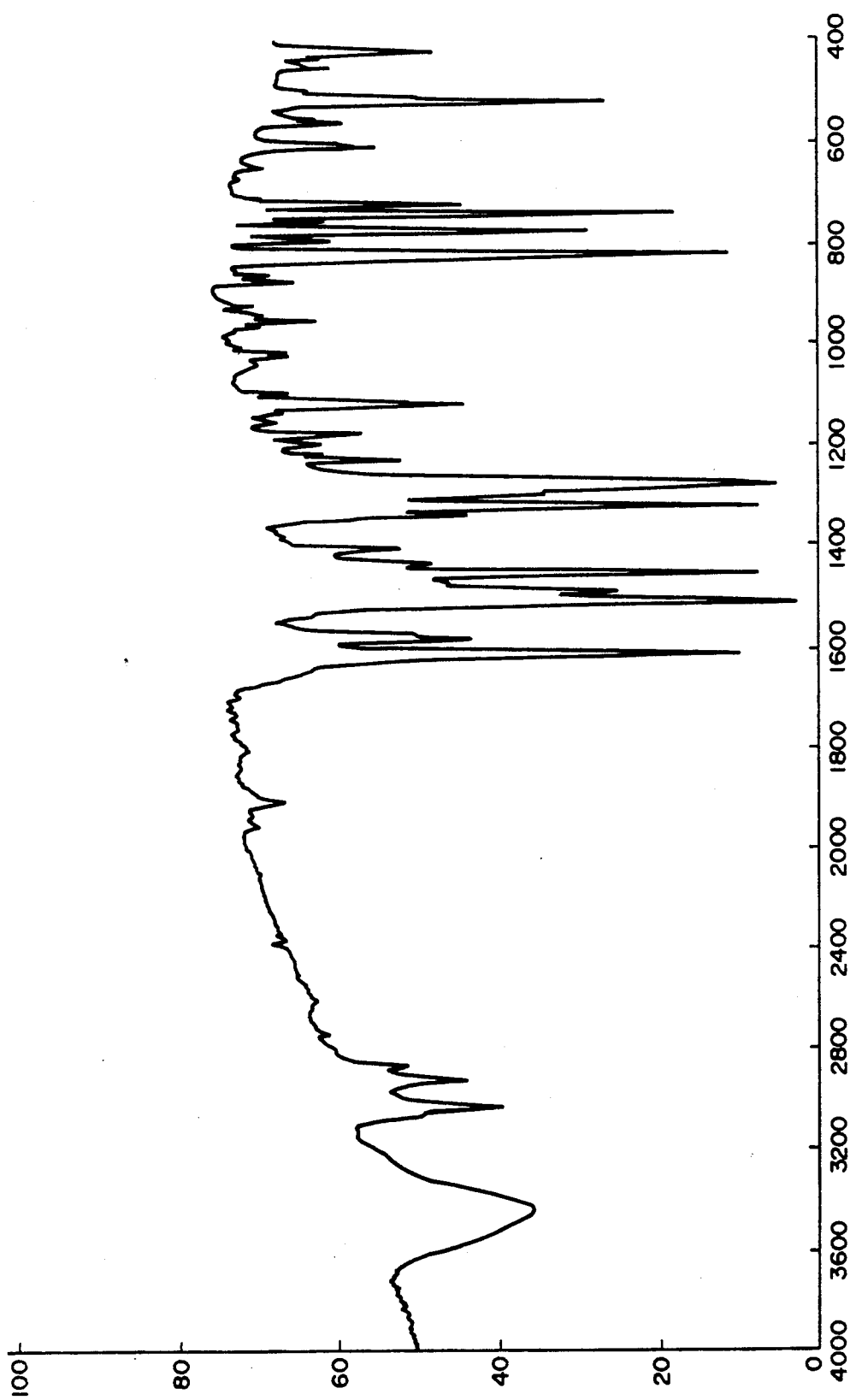
FIG. 1 shows an infrared spectrum of the fluorene compound No. 1 of the present invention.

In Formula (I), $R_1$ and $R_2$ each represent an alkyl group such as methyl, ethyl, propyl or butyl. $R_3$ represents a hydrogen atom, an alkyl group such as methyl, ethyl or propyl, an alkoxy group such as methoxy, ethoxy or propoxy, or a halogen atom such as chlorine, bromine or fluorine. $R_4$ and $R_5$ each represent a hydrogen atom, an alkyl group such as methyl, ethyl or propyl, an aralkyl group such as benzyl or phenethyl, or an aryl group such as phenyl or naphthyl.

The substituents $R_1$ and $R_2$ particularly govern the properties of the fluorene compound of the present invention. Particularly good sensitivity and durability are brought about when they are alkyl groups. Of the alkyl groups, the methyl group and the ethyl group are particularly preferred.

Of the fluorene compound represented by Formula (I), a fluorene compound represented by the following Formula (II) is more preferred.

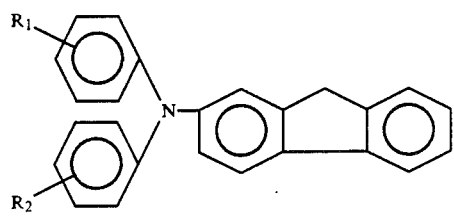

(II)

wherein $R_1$ and $R_2$ each represent a methyl group or an ethyl group.

Although the reason therefor is uncertain, it is presumed that, when $R_1$ and $R_2$ in the fluorene compound of the present invention are alkyl groups, its overlap with the charge-generating material or between fluorene compounds, or its orientation gives a steric advantage to, e.g., the movement of carriers, compared with other instances.

Typical examples of the compound represented by Formula (I) are listed below. The compound of the present invention, however, is by no means limited to these compounds.

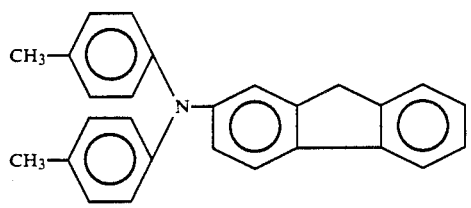

(1)

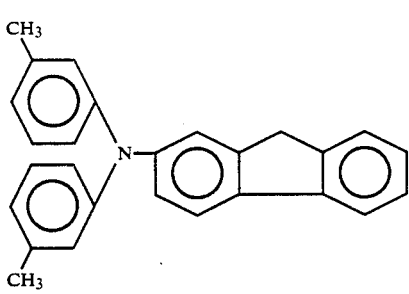

(2)

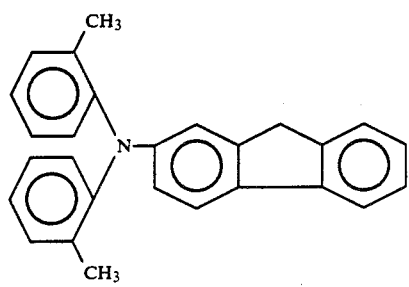

(3)

-continued

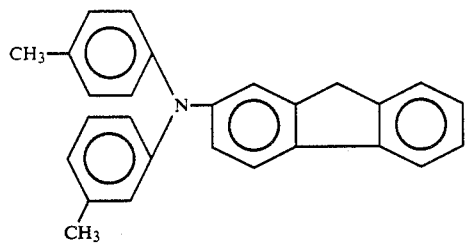

(4)

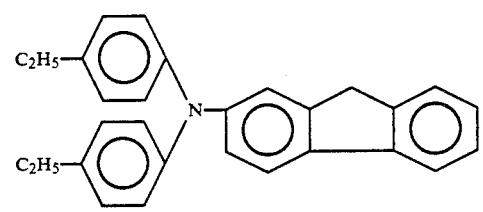

(5)

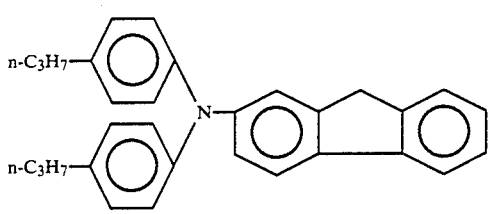

(6)

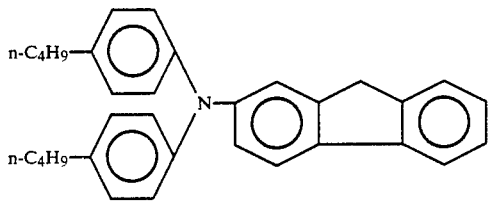

(7)

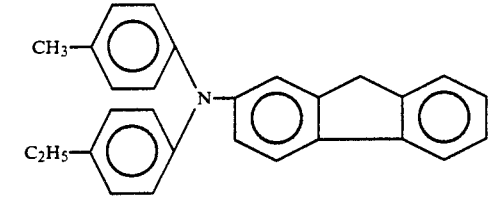

(8)

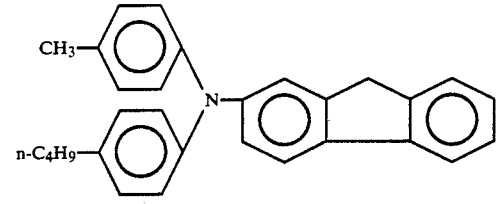

(9)

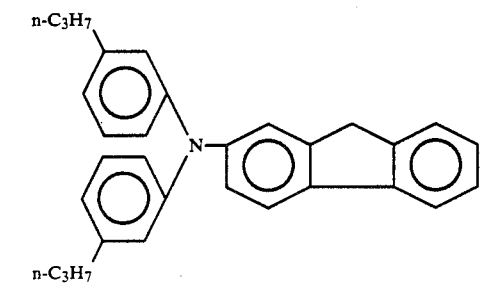

(10)

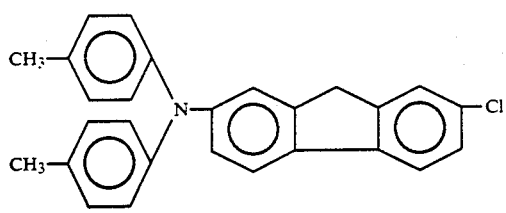 (11)
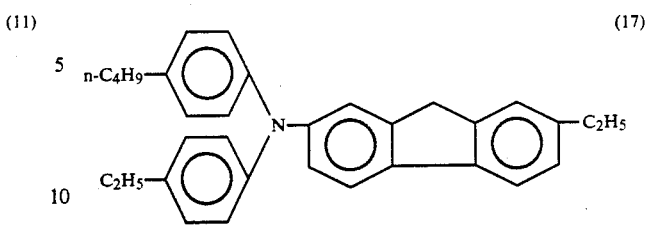 (17)
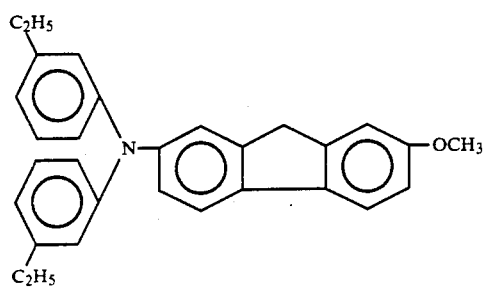 (12)
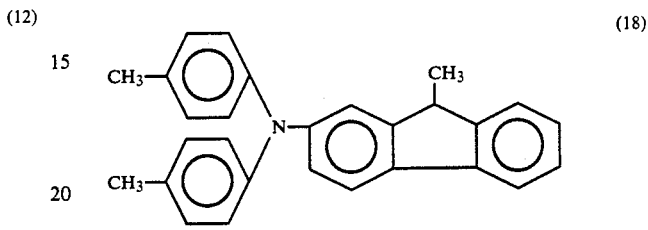 (18)
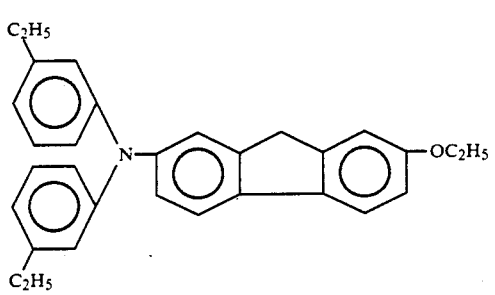 (13)
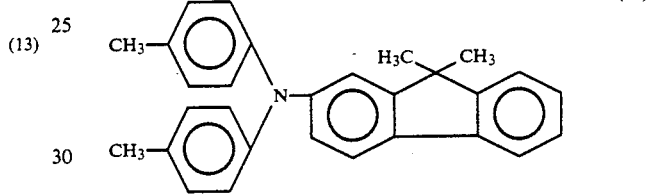 (19)
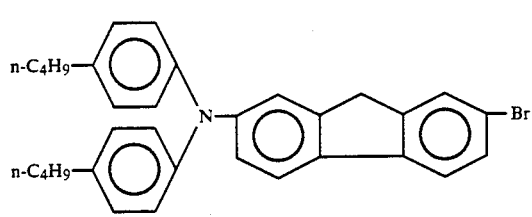 (14)
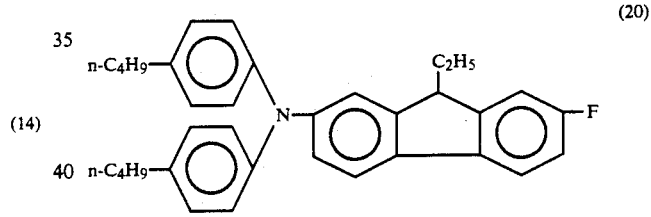 (20)
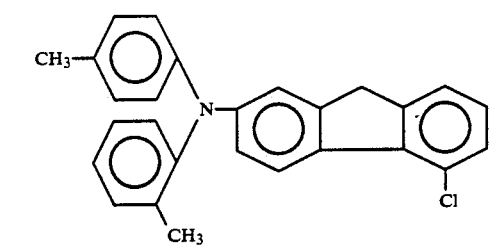 (15)
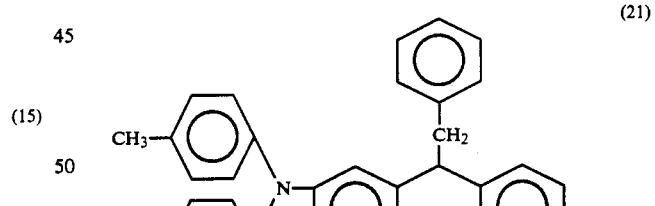 (21)
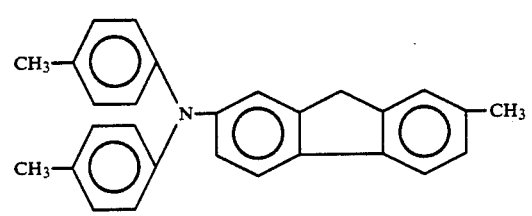 (16)
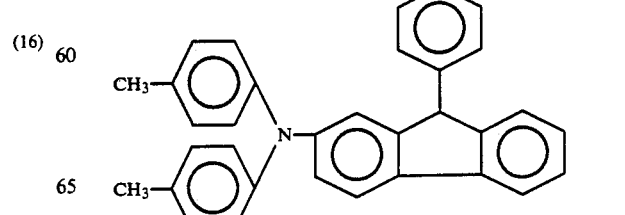 (22)

-continued

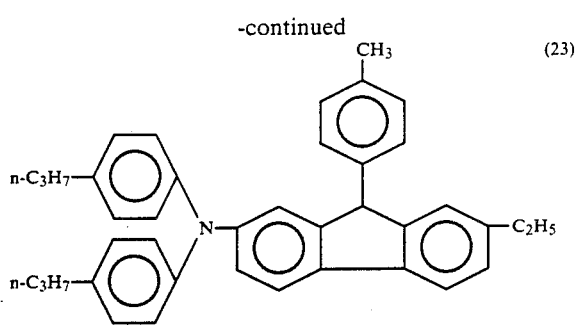
(23)

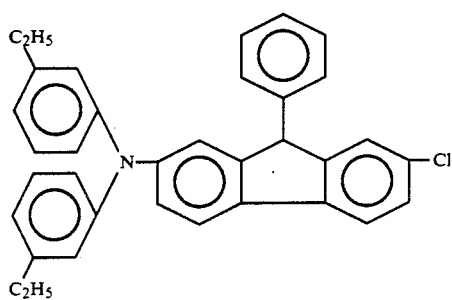
(24)

An example of the synthesis of the above compound will be shown below.

Synthesis of the exemplary compound No. (1)

In 20 ml of nitrobenzene, 10.0 g (55.2 mmol) of 2-aminofluorene, 36.1 g (165.6 mmol) of p-iodotoluene, 22.9 g (165.7 mmol) of anhydrous potassium carbonate and 7.0 g of copper powder were added, followed by heating under reflux for 8 hours with stirring. The reaction mixture was left to cool, and thereafter suction-filtered, followed by removal of the filtrate under reduced pressure. The residue was subjected to separation and purification using a silica gel column to give 15.6 g of an end compound (1) (yield: 78.2%).

The melting point was 126.0° to 126.5° C. Elementary analysis gave the following results as $C_{27}H_{23}N$

|  | C (%) | H (%) | N (%) |
| --- | --- | --- | --- |
| Calculated: | 89.71 | 6.41 | 3.88 |
| Found: | 89.69 | 6.45 | 3.86 |

FIG. 1 shows the infrared absorption spectrum of the compound thus synthesized (according to the KBr tablet method).

The electrophotographic photosensitive member of the present invention is basically comprised of a conductive support and a photosensitive layer provided thereon. This photosensitive layer contains the fluorene compound represented by the above Formula (I).

The photosensitive member may have the layer constitution with the form including the following:

(1) Conductive support/Layer containing the charge-generating material/Layer containing the charge-transporting material.

(2) Conductive support/Layer containing the charge-transporting material/Layer containing the charge-generating material.

(3) Conductive support/Layer containing the charge-generating material and charge-transporting material.

(4) Conductive support/Layer containing the charge-generating material and charge-transporting material.

The fluorene compound of the present invention, represented by Formula (I), has a high positive-hole transporting power, and can be used as the charge-transporting material in the photosensitive layers of the above forms. In the case when the photosensitive layer has the form (1), the photosensitive member is preferably used under negative charge; in the case of the form (2), under positive charge; and in the cases of the forms (3) and (4), under any of the positive charge and negative charge.

In the electrophotographic photosensitive member of the present invention, a suitable intermediate layer may be further provided between the conductive support and photosensitive layer, or a protective layer or an insulating layer may also be provided on the surface of the photosensitive layer, for the purpose of improving the adhesion or controlling the charge injection. The constitution of the photosensitive member of the present invention is by no means limited to the above fundamental constitution.

Of the above constitution, the form (1) is particularly preferred, and will be further detailed below.

The conductive support used in the present invention includes supports with the forms shown below:

(1) Metals such as aluminum, an aluminum alloy, stainless steel, and copper.

(2) Non-conductive supports such as glass, resin and paper or conductive supports of the above (1) on each of which a metal such as aluminum, palladium, rhodium, gold or platinum is deposited or laminated to form a thin film.

(3) Non-conductive supports such as glass, resin and paper or conductive supports of the above (1) on each of which a layer comprising a conductive compound such as a conductive polymer, tin oxide or indium oxide is formed by deposition or coating.

The conductive support may be in the shape of either a sheet or a drum.

Effective charge-generating materials used in the present invention include, for example, the following materials. These charge-generating materials may be used alone or in combination of two or more kinds.

(1) Azo pigments such as monoazo, bisazo or trisazo pigments.

(2) Phthalocyanine pigments such as metallic phthalocyanines and non-metallic phthalocyanines.

(3) Indigo pigments such as indigo and thioindigo.

(4) Perylene pigments such as perylenic acid anhydride and perylenic acid imide.

(5) Polycyclic quinone pigments such as anthraquinone and pyrenequinone.

(6) Squarilium coloring matters.

(7) Pyrylium salts and thiopyrylium salts.

(8) Triphenylmethane coloring matters.

(9) Inorganic materials such as selenium and amorphous silicon.

The layer that contains the charge-generating material, i.e, the charge-generation layer can be formed by dispersing the above-mentioned charge-generating material in a suitable binder, and coating the resulting dispersion on the conductive support. It can also be formed by forming a thin film on the conductive support by the dry method such as vacuum deposition, sputtering or CVD.

The above binder can be selected from binder resins of a broad range. It includes, for example, polycarbonate resins, polyester resins, polyacrylate resins, butyral resins, polystyrene resins, polyvinyl acetal resins, diallylphthalate resins, acrylate resins, methacrylate resins, vinyl acetate resins, phenol resins, silicone resins polysulfone resins, styrene-butadiene copolymer resins, alkyd resins, epoxy resins, urea resins, and vinyl chloride-vinyl acetate copolymer resins, to which, however, the binder is by no means limited. These may be used alone, or in a mixture of two kinds or more of these. The resin may be contained in the charge-generation layer in an amount of not more than 80% by weight, and preferably not more than 40% by weight. The charge-generation layer may have a film thickness of not more than 5 μm, and, in particular, may preferably be a thin film layer with a film thickness of from 0.01 μm to 1 μm.

Sensitizers of various types may also be added in the charge-generation layer.

The layer that contains the charge-transporting material, i.e.. the charge-transport layer can be formed by the combination of the fluorene compound represented by the above Formula (I) and any suitable binder resin. Here, the binder resin used in the charge-transport layer include the resins used in the above charge-generation layer, and may further include photoconductive polymers such as polyvinyl carbazole and polyvinyl anthracene.

The binder resin and the fluorene compound of the present invention may preferably be mixed in such a proportion that the fluorene compound is in an amount of from 10 to 500 parts by weight based on 100 parts by weight of the binder resin.

The charge-transport layer is electrically connected to the charge generation layer described above, and has the functions of receiving the charge carriers injected from the charge-generation layer in the presence of an electric field and also of transporting these charge carriers to the surface. This charge-transport layer has a limit in the capability of transporting the charge carriers, and hence can not have an unnecessarily large film thickness. It may preferably have a thickness of from 5 μm to 40 μm, and particularly from 10 to 30 μm.

Antioxidants, ultraviolet absorbents, plasticizers, or known charge-transporting materials may further be optionally added in the charge-transport layer.

In the formation of such a charge-transport layer, suitable organic solvents may be used, and the layer can be formed by coating methods such as dip coating, spray coating, spinner coating, roller coating, Mayer bar coating, and blade coating.

An intermediate layer having a barrier function and adhesion function may be provided between the conductive support and photosensitive layer.

In addition, a protective layer may be laminated on the surface of the photosensitive layer such as a layer of resin in which a conductive material may be dispersed, and the like.

The electrophotographic photosensitive member of the present invention can be not only utilized in electrophotographic copying machines, but also widely used in the field in which the electrophotography is applied, such as laser beam printers, CRT printers, LED printers. electrophotographic lithography systems.

FIG. 2 schematically illustrates the constitution of a transfer-type electrophotographic apparatus commonly used, in which a drum photosensitive member is used.

In FIG. 2, the numeral 1 denotes a drum photosensitive member serving as an image supporting member, which is rotated around a shaft 1a at a given peripheral speed in the direction shown by arrow. In the course of rotation, the photosensitive member 1 is uniformly charged on its periphery, with positive or negative given potential by the operation of a charging means 2, and then photoimagewise exposed to light L (slit exposure, laser beam scanning exposure, etc.) at an exposure area 3 by the operation of an imagewise exposing means (not shown). As a result, electrostatic latent images corresponding to the exposure images are successively formed on the periphery of the photosensitive member.

The electrostatic latent images thus formed are subsequently developed by toner by the operation of a developing means 4. The resulting toner-developed images are then successively transferred by the operation of a transfer means 5, to the surface of a transfer medium P fed from a paper feed section (not shown) to the part between the photosensitive member 1 and the transfer means 5 in the manner synchronized with the rotation of the photosensitive member 1.

The transfer medium P on which the images have been transferred is separated from the surface of the photosensitive member and led through an image-fixing means 8, where the images are fixed and then delivered to the outside as a transcript (a copy).

The surface of the photosensitive member 1 after the transfer of images is brought to removal of the toner remaining after the transfer, using a cleaning means 6. Thus the photosensitive member is cleaned on its surface and then repeatedly used for the formation of images.

The charging means 2 for giving uniform charge on the photosensitive member 1 include corona chargers, which are commonly put into wide use. As the transfer means 5, corona transfer units are also commonly put into wide use.

The electrophotographic apparatus may be constituted of a combination of plural components joined as one apparatus unit from among the constituents such as the above photosensitive member, developing means and cleaning means so that the unit can be freely mounted on or detached from the body of the apparatus. For example, the photosensitive member 1 and the cleaning means 6 may be joined into one apparatus unit so that the unit can be freely mounted or detached using a guide means such as a rail provided in the body of the apparatus. Here, the above apparatus unit may be so constituted as to be joined together with the charge means and/or the developing means.

EXAMPLES

The present invention will be described below in greater detail by giving Examples.

EXAMPLE 1

Using a sand mill, 5 g of a disazo pigment as the charge-generating material, represented by the following structural formula:

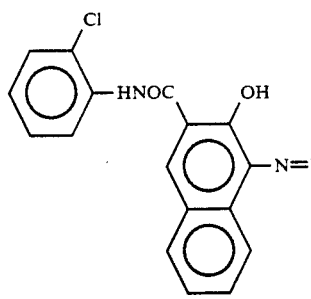
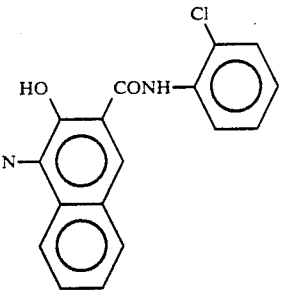

was dispersed for 24 hours together with a solution obtained by dissolving 2 g of butyral resin (degree of butyralation: 63 mol %) in 100 ml of cyclohexanone. A coating solution was thus prepared.

The resulting coating solution was applied to aluminum sheet so as to give a dry coating thickness of 0.2 μm to form a charge-generation layer.

Next, 10 g of the above exemplary compound No. (10) as the charge-transporting material and 10 g of polycarbonate resin (weight average molecular weight: 20,000) were dissolved in 70 g of monochlorobenzene. The resulting solution was coated on the charge-generation layer by Mayer bar coating to form a charge-transport layer with a dry coating thickness of 20 μm. An electrophotographic photosensitive member was thus prepared.

The electrophotographic photosensitive member thus prepared was subjected to corona charging at −5 kV according to a static method using an electrostatic copy paper tester Model-SP-428, manufactured by Kawaguchi Denki K.K., which was retained in the dark for 1 second and then exposed to light at an illumination of 20 lux to measure charge characteristics.

The surface potential (Vo) and the amount of exposure $E_{1/5}$) necessary for decaying to 1/5 the potential ($V_1$) after dark-decaying for 1 second was measured as the charging characteristics.

In order to further measure the fluctuation of light portion potential and dark portion potential after repeated use, the photosensitive member prepared in the present Example was stuck on a cylinder for a photosensitive drum of a PPC copying machine (NP-3525, manufactured by Canon Inc.), and the copying of 10,000 sheets was carried out using the same machine, to measure the fluctuation of light portion potential ($V_L$) and dark portion potential ($V_D$) observed at the initial stage and after the 10,000 sheet copying. The $V_D$ and $V_L$ at the initial stage were so set as to be −700 V and 200 V, respectively. Results obtained are shown in Table 1.

TABLE 1

| Example 1 | $V_0$ (V) | $V_1$ (V) | $E_{1/5}$ (lux · sec) | Initial potential (V) | After 10,000 sheet duration (V) |
|---|---|---|---|---|---|
| | −699 | −690 | 1.4 | $V_D$: −700 | −697 |
| | | | | $V_L$: −200 | −204 |

EXAMPLES 2 TO 12, COMPARATIVE EXAMPLES 1 TO 8

In each of the present examples, Example 1 was repeated to prepare electrophotographic photosensitive members, except that the exemplary compound No. (10) used in Example 1 as the charge-transporting material was replaced with the exemplary compound No. (1), (2), (5), (6), (7), (11), (13), (18), (20), (21) or (23), and a bisazo pigment of the following structural formula was used as the charge-generating material.

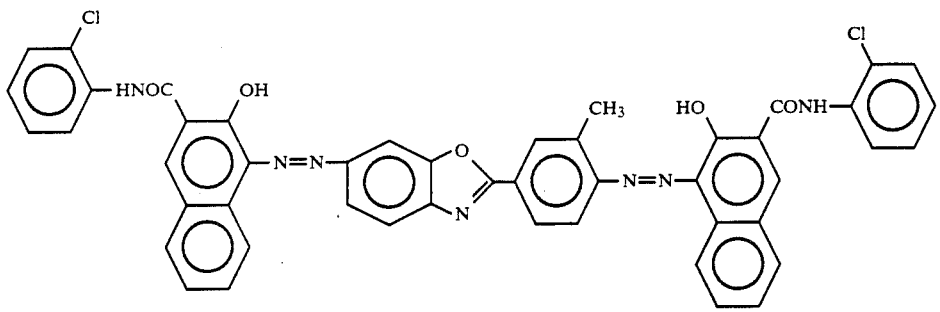

The electrophotographic performance of each photosensitive member was measured in the same manner as in Example 1. Results thus obtained are shown in Table 2.

For comparison, using the compounds of the following structural formulas, electrophotographic photosensitive members were prepared in the same manner as in the above, and the electrophotographic performance thereof was also measured. Results respectively obtained are shown in Table 3.

Comparative Compounds:

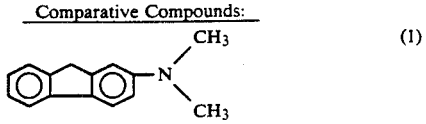

(1)

-continued
Comparative Compounds:

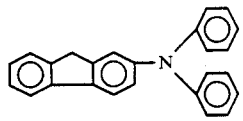 (2)

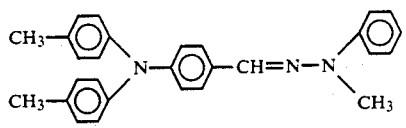 (8)

TABLE 2

| Example | Exemplary Comp. | $V_0$ (V) | $V_1$ (V) | $E_{1/5}$ (lux·sec) | Initial potential $V_D(V)$ | Initial potential $V_L(V)$ | After 10,000 sheet duration $V_D(V)$ | After 10,000 sheet duration $V_L(V)$ |
|---|---|---|---|---|---|---|---|---|
| 2 | (1) | −700 | −695 | 1.4 | −700 | −200 | −690 | −210 |
| 3 | (2) | −698 | −694 | 1.5 | −700 | −200 | −687 | −215 |
| 4 | (5) | −697 | −692 | 1.4 | −700 | −200 | −691 | −216 |
| 5 | (6) | −701 | −694 | 2.4 | −700 | −200 | −686 | −230 |
| 6 | (7) | −700 | −696 | 2.5 | −700 | −200 | −685 | −235 |
| 7 | (11) | −699 | −698 | 1.8 | −700 | −200 | −690 | −224 |
| 8 | (13) | −700 | −691 | 1.9 | −700 | −200 | −687 | −225 |
| 9 | (18) | −698 | −693 | 1.8 | −700 | −200 | −687 | −223 |
| 10 | (20) | −700 | −691 | 2.7 | −700 | −200 | −693 | −234 |
| 11 | (21) | −700 | −692 | 1.9 | −700 | −200 | −690 | −227 |
| 12 | (23) | −697 | −693 | 2.8 | −700 | −200 | −688 | −235 |

TABLE 3

| Comparative Example | Comparative Comp. | $V_0$ (V) | $V_1$ (V) | $E_{1/5}$ (lux·sec) | Initial potential $V_D(V)$ | Initial potential $V_L(V)$ | After 10,000 sheet duration $V_D(V)$ | After 10,000 sheet duration $V_L(V)$ |
|---|---|---|---|---|---|---|---|---|
| 1 | (1) | −701 | −686 | 6.9 | −700 | −200 | −654 | −251 |
| 2 | (2) | −698 | −690 | 3.9 | −700 | −200 | −765 | −315 |
| 3 | (3) | −698 | −685 | 3.1 | −700 | −200 | −545 | −245 |
| 4 | (4) | −699 | −695 | 6.8 | −700 | −200 | −721 | −320 |
| 5 | (5) | −700 | −691 | 5.9 | −700 | −200 | −649 | −311 |
| 6 | (6) | −700 | −691 | 3.0 | −700 | −200 | −611 | −301 |
| 7 | (7) | −701 | −690 | 4.2 | −700 | −200 | −624 | −360 |
| 8 | (8) | −697 | −682 | 2.8 | −700 | −200 | −589 | −259 |

As will be evident from Tables 2 and 3, the fluorene compound of the present invention is seen to be very superior in the sensitivity and the potential stability in repeated use, compared with the comparative compounds.

EXAMPLE 13

On an aluminum sheet, a solution obtained by dissolving 5 g of a methoxymethylated nylon resin (number average molecular weight: 32,000) and 10 g of an alcohol-soluble copolymer nylon resin (number average molecular weight: 29,000) in 95 g of methanol was coated by Meyer bar coating, followed by drying to form a subbing layer with a dry coating thickness of 1 μm.

Next, 10 g of a charge-generating material represented by the following structural formula:

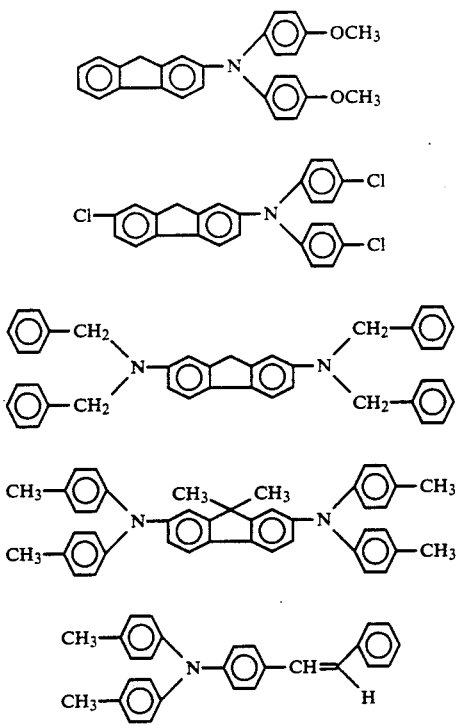

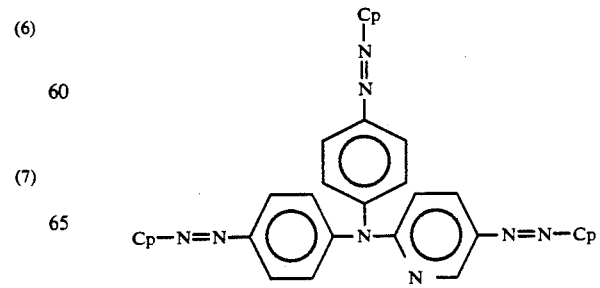

Cp = 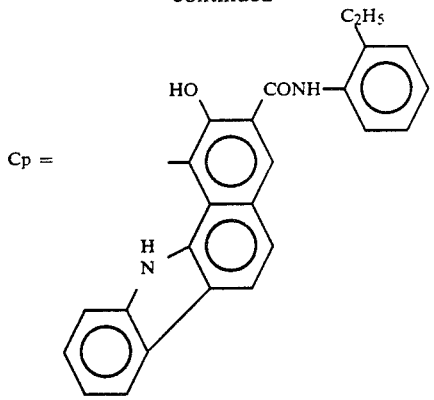

-continued butyral resin (degree of butyralation: 63 mol %) and 200 g of dioxane were dispersed for 48 hours using a ball mill dispersing machine. The resulting dispersion was coated on the subbing layer previously formed to form a charge generation layer with a dry coating thickness of 0.15 μm.

Next, 10 g of the above exemplary compound No. (4) and 10 g of polymethyl methacrylate resin (number average molecular weight: 50,000) were dissolved in 70 g of monochlorobenzene, and the resulting solution was coated on the charge generation layer previously formed, followed by drying to form a charge transport layer with a dry coating thickness of 19 μm. An electrophotographic photosensitive member was thus prepared.

On the photosensitive member thus prepared, corona discharging at −5 kV was carried out. The surface potential produced at this time (initial potential $V_0$) was measured. Further measured were the surface potential after this photosensitive member was left to stand in the dark for 1 second. The sensitivity was evaluated by measuring the amount of exposure $E_{1/5}$ μJ/cm$^2$) necessary for decaying to 1/5 the potential $V_1$ after dark-decaying for 1 second. Here, a gallium/aluminum/arsenic three component semiconductor laser (output: 5 mW; oscillation wavelength: 780 nm) was used as a light source. Results obtained were as follows.

| $V_0$ | −700 V |
|---|---|
| $V_1$ | −695 V |
| $E_{1/5}$ | 1.01 μJ/cm$^2$ |

Next, the above photosensitive member was set in a laser beam printer (LBP-CX, manufactured by Canon Inc.) which is a printer of a reversal development type electrophotographic system, equipped with the same semiconductor laser as the above, to carry out tests of actual image formation. Conditions were as follows:

Surface potential after primary charging: −700 V;

surface potential after imagewise exposing: −150 V (amount of exposure: 2.0 μJ/cm$^2$); transfer potential: +700 V; polarity of developer: negative; processing speed: 50 mm/sec.; development condition developing bias): −450 y; imagewise exposing scan system: image scanning; exposure to light before primary charging: red and whole-areal exposure of 50 lux·sec. Image formation was carried out by line-scanning the laser beam according to character signals and image signals, obtaining good prints in both characters and images.

Images were further produced continuously on 3,000 sheets. As a result, good prints were obtained until 3,000 sheet copying from the initial stage.

EXAMPLES 14 TO 17, COMPARATIVE EXAMPLES 9 TO 10

A solution obtained by mixing 1 part by weight of dibromoanthanthrone represented by the following structural formula:

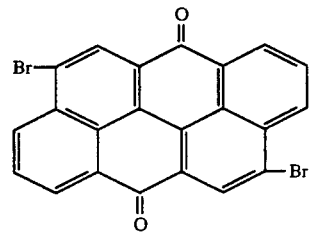

and 0.5 part by weight of polycarbonate resin into 100 parts by weight of 1,2-dichloroethane and dispersing the resulting mixture for 30 hours using a ball mill, was coated on an aluminum sheet by Mayer bar coating so as to give a dry coating thickness of 0.8 μm. A charge-generation layer was thus formed.

Next, a charge-transport layer was formed in the same manner as in Example i except that the above exemplary compounds Nos. (1), (8), (14) and (19) were each used. The photosensitive members thus obtained were evaluated in the like manner.

For comparison, electrophotographic photosensitive members were prepared in the like manner, using a charge-transporting materials the above comparative compound No. (2) and the compound No. (9) of the following structural formula:

(9)

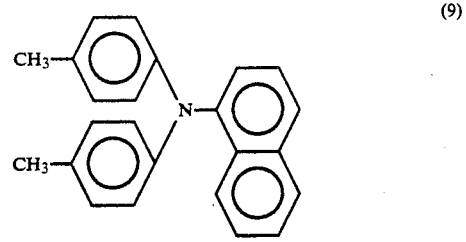

The electrophotographic performances of the electrophotographic photosensitive members thus prepared were measured. The results obtained are shown in tables 4 and 5.

TABLE 4

| Example | Exemplary Comp. | $V_0$ (V) | $V_1$ (V) | $E_{1/5}$ (lux · sec) | Initial potential | | After 10,000 sheet duration | |
|---|---|---|---|---|---|---|---|---|
| | | | | | $V_D(V)$ | $V_L(V)$ | $V_D(V)$ | $V_L(V)$ |
| 14 | (1) | −700 | −695 | 2.3 | −700 | −200 | −694 | −212 |
| 15 | (8) | −698 | −694 | 2.4 | −700 | −200 | −695 | −215 |
| 16 | (14) | −697 | −691 | 3.9 | −700 | −200 | −690 | −224 |

TABLE 4-continued

| Example | Exemplary Comp. | $V_0$ (V) | $V_1$ (V) | $E_{1/5}$ (lux·sec) | Initial potential $V_D(V)$ | Initial potential $V_L(V)$ | After 10,000 sheet duration $V_D(V)$ | After 10,000 sheet duration $V_L(V)$ |
|---|---|---|---|---|---|---|---|---|
| 17 | (19) | −697 | −695 | 2.6 | −700 | −200 | −691 | −227 |

TABLE 5

| Comparative Example | Comparative Comp. | $V_0$ (V) | $V_1$ (V) | $E_{1/5}$ (lux·sec) | Initial potential $V_D(V)$ | Initial potential $V_L(V)$ | After 10,000 sheet duration $V_D(V)$ | After 10,000 sheet duration $V_L(V)$ |
|---|---|---|---|---|---|---|---|---|
| 9 | (2) | −699 | −690 | 4.9 | −700 | −200 | −740 | −345 |
| 10 | (9) | −698 | −691 | 5.6 | −700 | −200 | −665 | −319 |

EXAMPLE 18

Into 100 g of a toluene (50 parts by weight)/dioxane (50 parts by weight) solution of polyester resin (weight average molecular weight: 49,000), 3 g of 4-(4-diemthylaminophenyl)-2,6-diphenylthiapyrylium perchlorate and 5 g of the exemplary compound No. (23) were mixed, and the mixture was dispersed for 6 hours using a ball mill. The resulting dispersion was coated on an aluminum sheet by Meyer bar coating, followed by drying at 100° C. for 2 hours. The photosensitive member thus prepared was measured in the same manner as in Example 1. Results obtained are shown below.

| | |
|---|---|
| $V_0$ | −700 V |
| $V_1$ | −694 V |
| $E_{1/5}$ | 3.3 lux·sec |
| Initial potential | |
| $V_D$ | −700 V |
| $V_L$ | −200 V |
| After 10,000 sheet duration | |
| $V_D$ | −690 V |
| $V_L$ | −224 V |

EXAMPLES 19

On an aluminum sheet, an aqueous ammonium solution of casein (casein: 11.2 g; 28% ammonia water: 1 g; water: 222 ml) was coated by Meyer bar coating to form a subbing layer with a dry coating thickness of 1 μm. The charge-transport layer and charge-generation layer as in Example 5 were successively laminated thereon. Thus, a photosensitive member was formed in entirely the same manner as in Example 1 except for the difference in the layer constitution. Then the charge characteristics were measured in the same manner as in Example 1, provided that the charge polarity was changed to ⊕. Results thus obtained are shown below.

| | |
|---|---|
| $V_0$ | +690 V |
| $V_1$ | +680 V |
| $E_{1/5}$ | 4.1 lux·sec |

EXAMPLE 20

A 5% methanol solution of a soluble nylon (6-66-610-12 nylon four-component copolymer) was coated on an aluminum sheet to form a subbing layer with a dry thickness of 0.5 μm.

Next, 5 g of a pigment represented by the following structural formula:

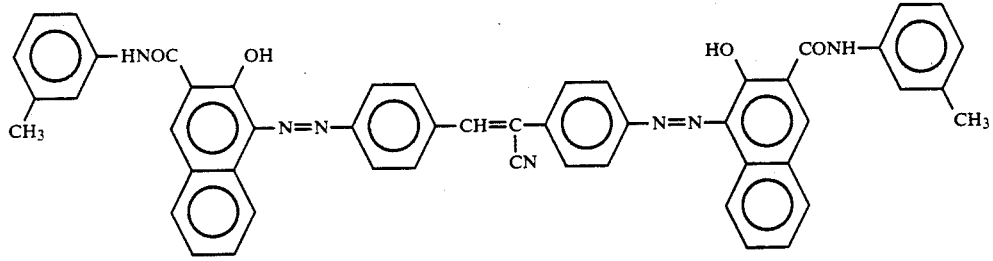

was dispersed in 95 ml of tetrahydrofuran, using a sand mill. Then a solution obtained by dissolving 5 g of the above exemplary compound No. (4) and 10 g of bisphenol Z type polycarbonate resin (weight average molecular weight: 50,000) in 30 ml of monochlorobenzene was added in the dispersion previously prepared, which was dispersed for further 2 hours. The resulting dispersion was coated by Mayer bar coating on the subbing layer previously formed so as to give a dry coating thickness of 20 μm, followed by drying. The electrophotographic performance of the photosensitive member thus prepared was measured in the same method as in Example 1. Results thus obtained are shown below.

| | |
|---|---|
| $V_0$ | −698 V |
| $V_1$ | −690 V |
| $E_{1/5}$ | 3.9 lux·sec |

We claim:

1. An electrophotographic photosensitive member comprising a conductive support and a photosensitive layer provided thereon, wherein said photosensitive layer contains a fluorene compound represented by the following Formula (I):

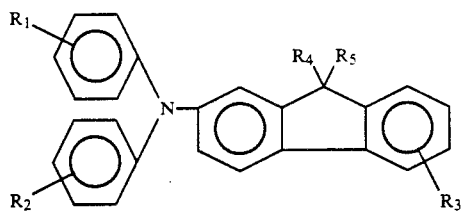

wherein $R_1$ and $R_2$ each represent an alkyl group; $R_3$ represents a hydrogen atom, an alkyl group, an alkoxy group or a halogen atom; $R_4$ and $R_5$ each represent a hydrogen atom, an alkyl group, an aralkyl group or an aryl group.

2. An electrophotographic photosensitive member according to claim 1, wherein, in the fluorene compound represented by Formula (I), $R_1$ and $R_2$ are methyl groups or ethyl groups.

3. An electrophotographic photosensitive member according to claim 1, wherein the fluorene compound represented by Formula (I) is a fluorene compound represented by the following Formula (II).

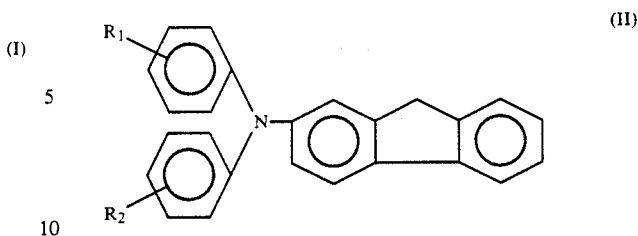

wherein $R_1$ and $R_2$ each represent a methyl group or an ethyl group.

4. An electrophotographic photosensitive member according to claim 1, wherein said photosensitive layer comprises a charge-generation layer provided on said conductive support, and a charge-transport layer provided on said charge-generation layer.

5. An electrophotographic photosensitive member according to claim 1 wherein said photosensitive layer comprises a charge-transport layer provided on said conductive support, and a charge-generation layer provided on said charge-transport layer.

6. An electrophotographic photosensitive member according to claim 1, wherein an intermediate layer is provided between said conductive support and photosensitive layer.

7. An electrophotographic photosensitive member according to claim 1, wherein a protective layer is provided on the surface of the photosensitive layer.

* * * * *

UNITED STATES PATENT AND TRADEMARK OFFICE
CERTIFICATE OF CORRECTION

PATENT NO. : 5,098,809
DATED : March 24, 1992
INVENTOR(S) : TOSHIHIRO KIKUCHI, ET AL.

It is certified that error appears in the above-identified patent and that said Letters Patent is hereby corrected as shown below:

Title page:

IN [54] TITLE

"FLUORINE" should read --FLUORENE--.

COLUMN 1

Line 4, "FLUORINE" should read --FLUORENE--.
Line 30, "weight" should read --weight,--.
Line 52, "power" should read --power,--.
Line 56, "rial" should read --rials--.
Line 58, "drozone" should read --drazone--.

COLUMN 9

Line 2, "resins poly-" should read --resins, poly- --.

COLUMN 11

Line 53, "sure $E_{1/5}$)" should read --sure ($E_{1/5}$)--.

COLUMN 15

Line 39, "exposure $E_{1/5} \mu J/cm^2$)" should read --exposure ($E_{1/5}$, $\mu J/cm^2$)--.
Line 42, "three component" should read --three-component--.

COLUMN 16

Line 2, ".-450 y;" should read -- -450 V;--.
Line 35, "Example i" should read --Example 1--.
Line 40, "a" should read --as--.
Line 58, "ta-" should read --Ta- --.

UNITED STATES PATENT AND TRADEMARK OFFICE
CERTIFICATE OF CORRECTION

PATENT NO. : 5,098,809
DATED : March 24, 1992
INVENTOR(S) : TOSHIHIRO KIKUCHI, ET AL.

Page 2 of 2

It is certified that error appears in the above-identified patent and that said Letters Patent is hereby corrected as shown below:

COLUMN 17

Line 22, "4-(4-diem-" should read --4-(4-dime- --.

COLUMN 19

Line 30, "Formula (II)." should read --Formula (II):--.

COLUMN 20

Line 16, "support," should read --support--.
    Line 19, "claim 1" should read --claim 1,--.
    Line 21, "support," should read --support--.

Signed and Sealed this

Seventeenth Day of August, 1993

Attest:

BRUCE LEHMAN

*Attesting Officer*      Commissioner of Patents and Trademarks